United States Patent
Pruter

(10) Patent No.: US 6,296,614 B1
(45) Date of Patent: Oct. 2, 2001

(54) NEEDLE GUIDE FOR ATTACHMENT TO ULTRASOUND TRANSDUCER PROBE

(76) Inventor: Rick L. Pruter, 611 Southgate Ave., Iowa City, IA (US) 52240-2166

( * ) Notice: Subject to any disclaimer, the term of this patent is extended or adjusted under 35 U.S.C. 154(b) by 0 days.

(21) Appl. No.: 09/526,048

(22) Filed: Mar. 15, 2000

Related U.S. Application Data

(63) Continuation-in-part of application No. 29/103,098, filed on Apr. 8, 1999, now Pat. No. Des. 424,693.

(51) Int. Cl.$^7$ .................................................. A61B 8/00
(52) U.S. Cl. ................................................. 600/461
(58) Field of Search ................................ 600/461, 462, 600/437, 463, 464

(56) References Cited

U.S. PATENT DOCUMENTS

| | | |
|---|---|---|
| D. 383,968 | 9/1997 | Bidwell et al. . |
| 2,451,183 | 10/1948 | Tantimonaco . |
| 2,536,963 | 1/1951 | Stephens . |
| 3,017,887 | 1/1962 | Heyer . |
| 3,538,915 | 11/1970 | Frampton et al. . |
| 3,556,079 | 1/1971 | Omizo . |
| 4,029,084 | 6/1977 | Soldner . |
| 4,058,114 | 11/1977 | Soldner . |
| 4,108,165 | 8/1978 | Kopp et al. . |
| 4,132,496 | 1/1979 | Casto . |
| 4,249,539 | 2/1981 | Vikomerson et al. . |
| 4,289,139 | 9/1981 | Enjoji et al. . |
| 4,332,248 | 6/1982 | DeVitis . |
| 4,363,326 | 12/1982 | Kopel . |
| 4,402,324 | 9/1983 | Lindgren et al. . |
| 4,408,611 | 10/1983 | Enjoji . |
| 4,469,106 | 9/1984 | Harui . |
| 4,489,730 | 12/1984 | Jingu . |
| 4,491,137 | 1/1985 | Jingu . |
| 4,497,325 | 2/1985 | Wedel . |
| 4,504,269 | 3/1985 | Durand . |
| 4,542,747 | 9/1985 | Zurinski et al. . |
| 4,635,644 | 1/1987 | Yagata . |
| 4,781,067 | 11/1988 | Cichanski . |
| 4,898,178 | 2/1990 | Wedel . |

(List continued on next page.)

OTHER PUBLICATIONS

Disposable Transrectal Needle Guide, Civco Medical Instruments Co., Inc. Medical Parkway, 102 Highway 1 South Kalona, IA 52247.

Maggi & Maggi II Plus, Sterile General Purpose Biopsy Needle Guides, Civco Medical Instrument Co., Inc. Medical Parkway, 102, Highway 1 South Kalona, IA 52247.

Ultra–Pro Sterile General Purpose Biopsy Needle Guide, Civco Medical Instruments, Co., Inc. Medical Parkway, 102 Highway 1 South Kalona, IA 52247.

(List continued on next page.)

*Primary Examiner*—Marvin M. Lateef
*Assistant Examiner*—Maulin Patel
(74) *Attorney, Agent, or Firm*—Allan L. Harms

(57) ABSTRACT

A versatile needle guide for attachment to an ultrasound transducer probe. The needle guide includes an open topped generally vertical passageway formed between a base member and a gauge top which is hingedly mounted to the base member. A spring urges a grooved face on the gauge top into abutment with a flat face on the base member. The gauge top may be pivoted about the hinge mounting to separate the grooved face from the flat face to open the side of the passageway to allow a needle to be removed from the needle guide. The gauge top may be easily disassembled from the base for interchange with another gauge top having a different size of groove.

15 Claims, 4 Drawing Sheets

U.S. PATENT DOCUMENTS

| | | |
|---|---|---|
| 4,970,907 | 11/1990 | Flynn . |
| 5,052,396 | 10/1991 | Wedel et al. . |
| 5,076,279 * | 12/1991 | Arenson et al. .................. 600/462 |
| 5,161,764 | 11/1992 | Roney . |
| 5,758,650 * | 6/1998 | Miller et al. .................... 600/461 |
| 6,203,499 * | 3/2001 | Imling et al. ................... 600/461 |

OTHER PUBLICATIONS

Aloka Needle Guide/Probe Cover Kits, Civco Medical Instruments Co., Inc. Medical parkway, 102 Highway 1 South Kalona, IA 52247.

Multi Pro 2000, Multi–Purpose Ultrasound Linear Tracking Instrument, Civco Medical Instruments Co., Inc. 418 B Avenue, Kalona, IA 52247.

"The Ultimate Guide in Ultrasound" advertising, Civco Medical Instruments Co., Inc., 418 B Avenue, Kalona, IA 52247.

"Hitting the Mark with Realtime Guidance", Civco PROgram, Drawer Q. Kalona, IA 52247.

* cited by examiner

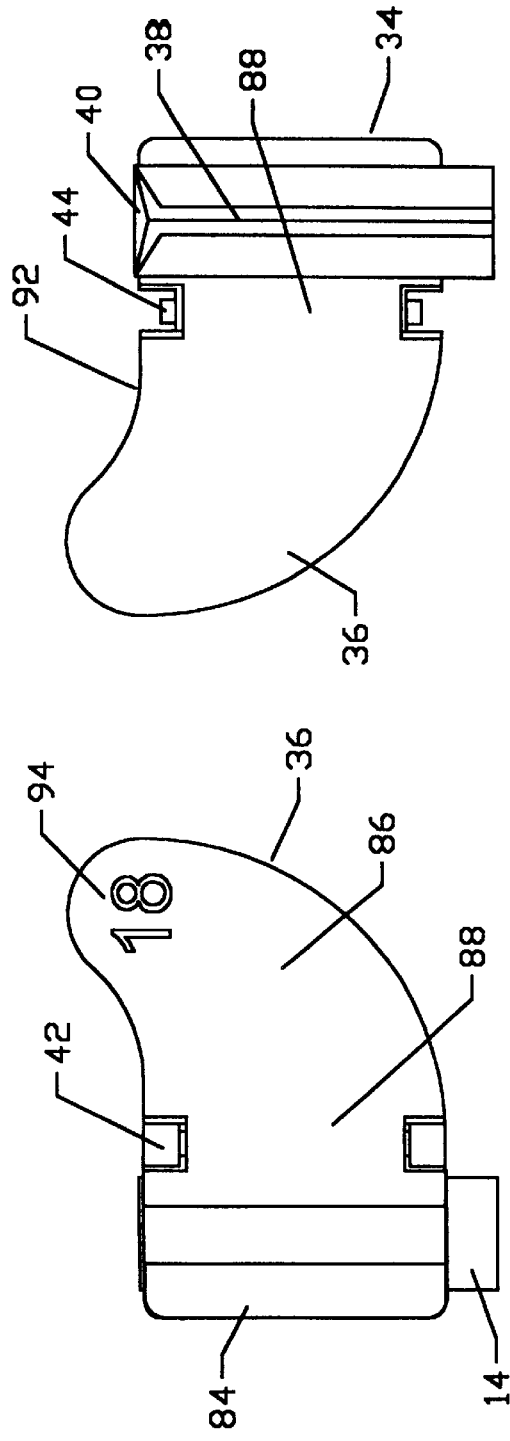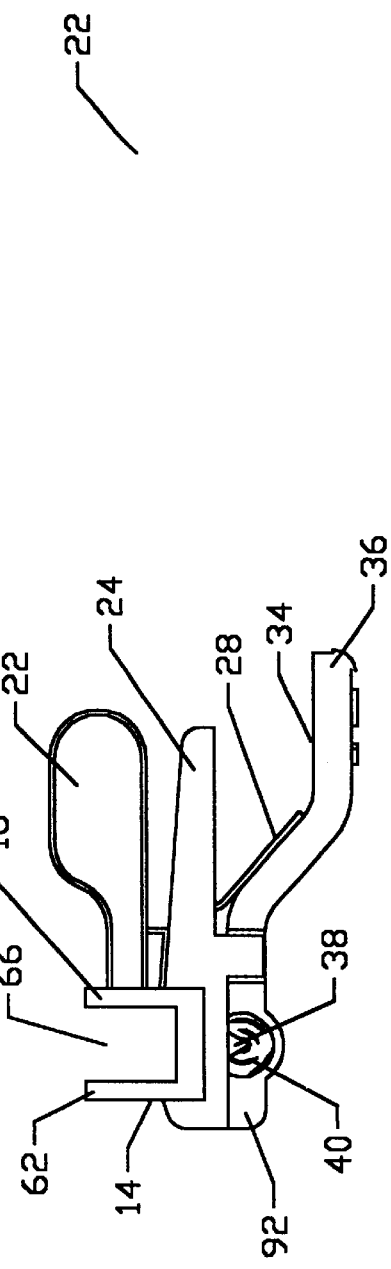

NEEDLE GUIDE FOR ATTACHMENT TO ULTRASOUND TRANSDUCER PROBE

CROSS REFERENCES

This is a continuation-in-part of Ser. No. 29/103,098, filed Apr. 8, 1999, now Des. Pat. No. 424,693.

BACKGROUND

In the field of medicine, procedures are done to obtain biopsy samples or to place drainage tubes within the body. To assist in such procedures, an ultrasound image may be obtained to guide the biopsy needle or drainage tube into proper position. Ultrasound imaging of this sort is accomplished by use of an ultrasound transducer probe touching the body near the location for puncture of the skin and tissues by the needle or cannula. In order to assist in placement of the needle or tube, needle guides have been developed to fastened to or be incorporated within the ultrasound transducer probe. The biopsy needle or drainage cannula can be guided by the attached or incorporated guide. Many of such prior art devices either require the needle to remain attached to the transducer until the needle is withdrawn from the body or else they utilize traps or complex pathways for the needle to travel to be released from the transducer probe after the transducer probe is no longer needed. Such prior art devices result in the operator having to keep the transducer resting on the body while the biopsy sample is retrieved or else they give rise to discomfort for the patient and inconvenience for the physician performing the procedure while disconnecting the placed needle or cannula from the ultrasound transducer probe.

SUMMARY OF THE INVENTION

It is an object of the present invention to provide a needle guide which allows easy release of a biopsy needle from an ultrasound transducer probe after the needle has been guided into place by visualization of ultrasound images generated by use of the ultrasound transducer probe.

The needle guide snaps onto the ultrasound transducer probe and may be removed by hand operation. The needle guide includes a passageway through which a biopsy needle may be passed to aim it into the body at a target location. The needle guide is formed such that the passageway directs the leading end of the biopsy needle into the image field of the transducer probe. The user may cause the needle guide to release the biopsy needle bilaterally by squeezing one side of the needle guide with the thumb and forefinger.

A mounting bracket which is retained to the ultrasound transducer probe includes a band snugly surrounding the probe such that its transmission face is not obstructed. The band includes a generally elongate protrusion, to which the needle guide member may be frictionally or mechanically retained such that the needle guide may be removed by manual effort without the use of tools. The needle guide includes a mounting body equipped with a pair of rails which receive the protrusion on the band around the transducer wand. A rotatable lock lever is rotatively operated to insert a blade through a slot in one rail to impinge the blade upon the protrusion.

The base member is fashioned to allow it to be snap fitted to the mounting body and to fit on the mounting body in a defined orientation. The base is equipped with a flat face adjacent a hinge element comprising spaced ears with indentations which become part of a hinge when a gauge top member is mounted to the base member. A gauge top member has a wall with a triangular groove which abuts the flat face of the base member when longitudinally spaced stubs on the gauge top member are captured in the indentations in the opposing ears of the base member. The stubs serve as an axis about which the gauge top member may pivot on the base member over a limited range. A spring is interposed between the base and the gauge top member to urge the grooves containing wall of the gauge top member to remain in abutment with the flat face of the base member.

The gauge top includes a handle which may be depressed toward the base against the bias of the spring in order to move the groove away from the flat face such that a needle which has been passed through the passageway may be released from the needle guide.

It is a further object of the invention to provide a disposable needle guide for attachment to a transducer probe which facilitates removal of the ultrasound transducer probe from a needle which has been passed through the needle guide.

It is also an object of the invention to provide a needle guide constructed of stainless steel which may be sterilized and reused.

It is a further object of the invention to provide a needle guide which may be easily disassembled to permit use of different diameter needles or cannula by exchanging only the outermost member of the needle guide without disengaging the remaining parts of the needle guide from the transducer probe.

It is another object to provide a needle guide which may be mounted to varying shapes of ultrasound transducer probes by use of a flexible or elastic strap.

It is a further object of the Invention to provide a needle guide for fixed attachments to an ultrasound transducer probe which permits release of a needle from the needle guide with the use of a user's thumb and forefinger of one hand.

It is also an object of the invention to provide a one piece assembled needle guide which is ready for use after mounting to a bracket on a transducer probe.

It is another object to provide a needle guide which has a funnel-shaped opening to facilitate insertion of the tip of a biopsy needle into the guide.

It is yet a further object of the invention to provide a needle guide for mounting to a transducer probe which has a rounded lower surface to reduce discomfort of patients who are touched by the guide.

These and other advantages and objects of the invention will be understood through examination of the detailed description which follows.

DESCRIPTION OF THE DRAWING FIGURES

FIG. 3 is a front elevation of the needle guide shown detached from the mounting bracket thereof.

FIG. 4 is a top plan view of the needle guide detached from the mounting bracket thereof.

FIG. 5 is a rear elevation of the gauge top member of the needle guide.

DETAILED DESCRIPTION OF THE INVENTION

Figure 1:
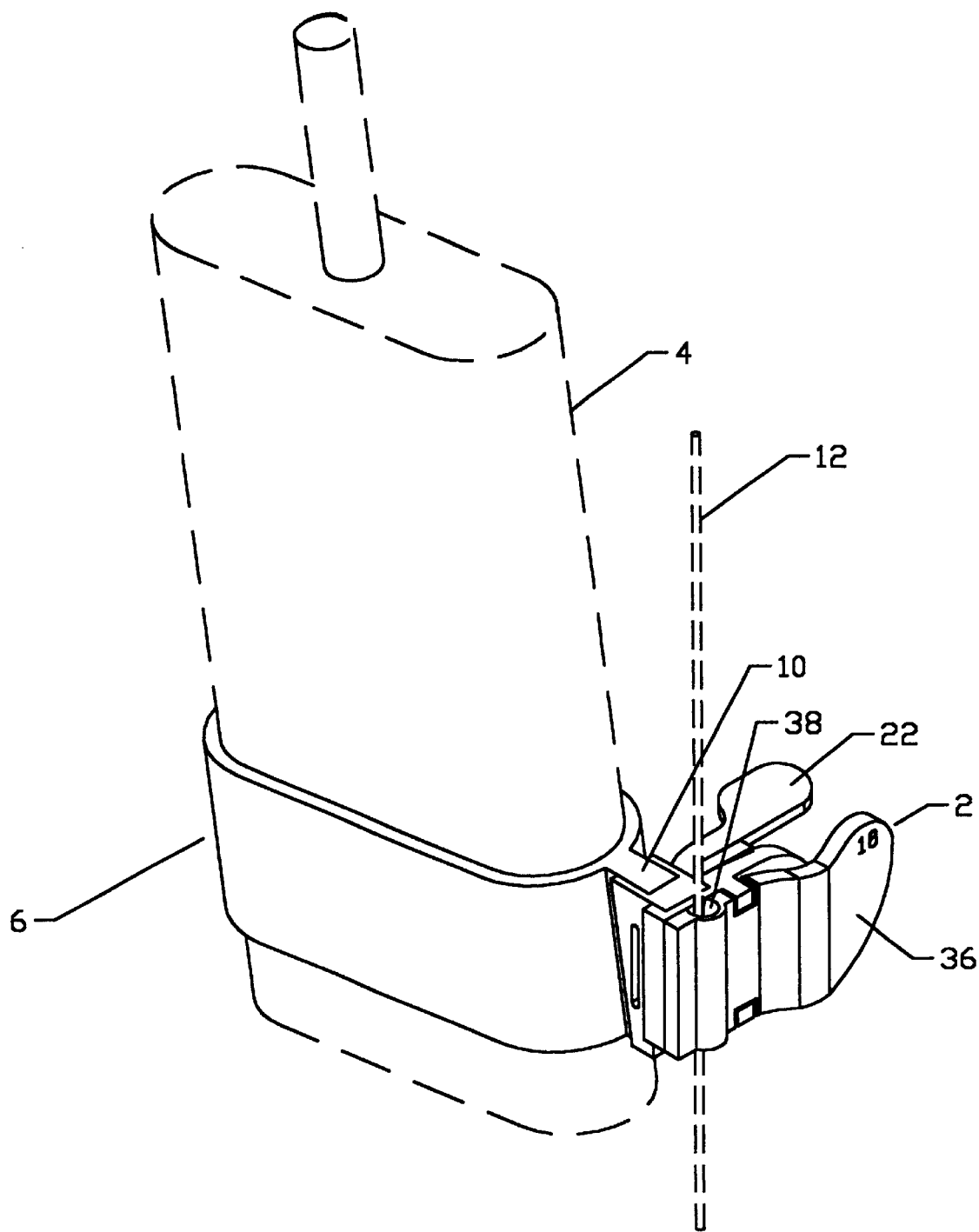
FIG. 1 is a perspective view of the preferred embodiment needle guide retained to an ultrasound transducer probe and having a needle passing thorough the barrel of the needle guide.
Figure 2:
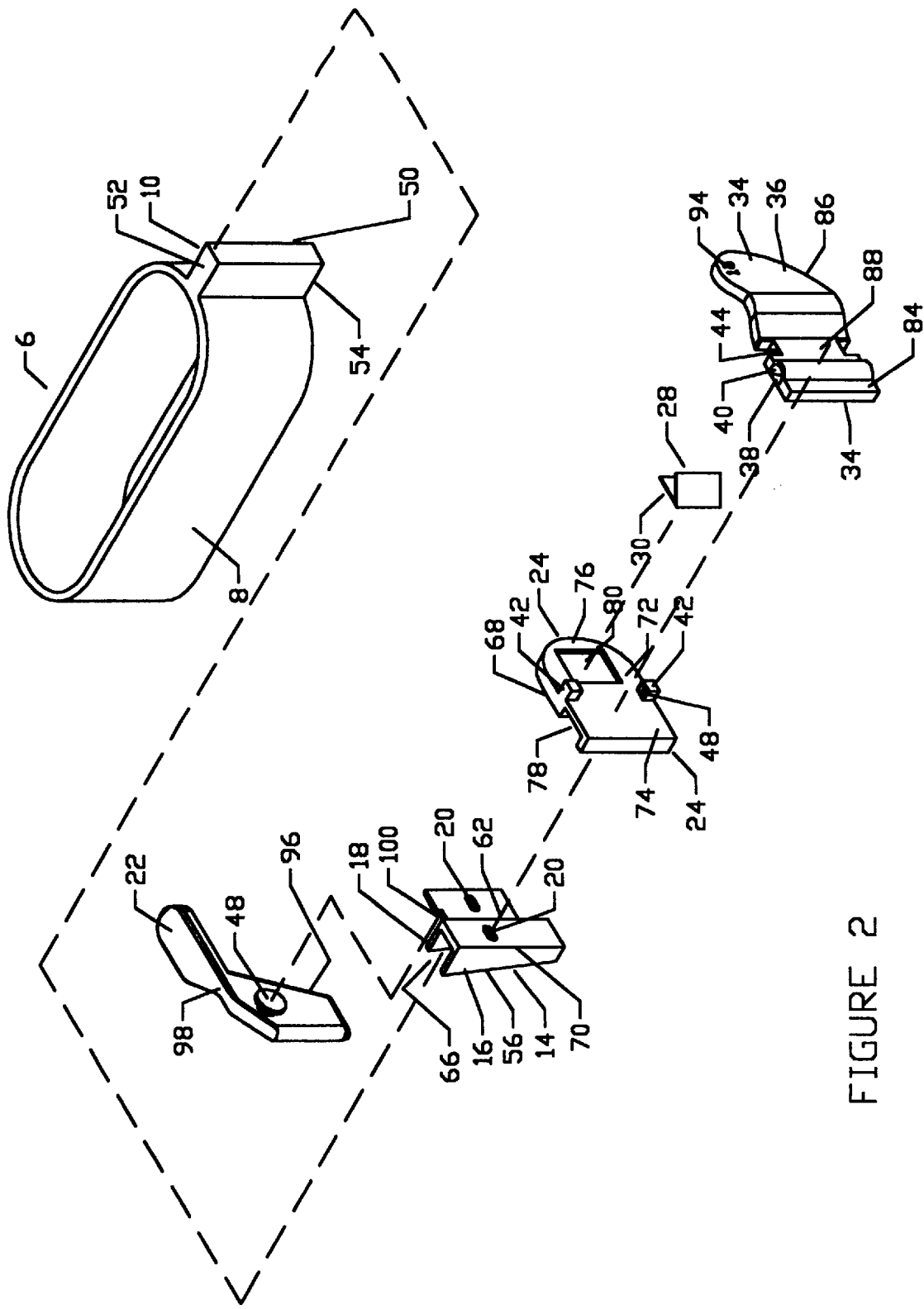
FIG. 2 is an exploded view in perspective of the preferred embodiment needle guide.

FIG. 1 shows the preferred embodiment needle guide 2 mounted to a mounting bracket 6 fixed to an ultrasound transducer probe 4. A biopsy needle 12 is shown being guided by needle guide 2 at an angle such that the lower end of the needle 12 will intersect the vertical axis of the probe 4. By so guiding the needle 12, the needle guide 2 allows the lower end of the needle 12 to enter the image field of the transducer probe 4 such that the operator of the instrument may position the lower tip of the needle at a location being viewed on the ultrasound imaging system of which transducer probe 4 is a part.

The needle guide 2 is mounted to a protrusion 10 which is formed on band 8 of mounting bracket 6. In the configuration shown in FIG. 1, the band 8 surrounds and conforms to the shape of the generally rectangular transducer probe 4. Band 8 may be fabricated of a flexible material such that it may be fitted conformingly to other shapes of transducer probe but it is to be understood that band 8 must fit tightly around the transducer probe 4 such that it will remain firmly in position during use of the needle guide 2. Band 8 may also be constructed as a belt or strap, the ends of which may be joined by hook and loop fasteners, or by buckle, or hook and catch fastening means.

Preferably needle guide 2 is fabricated from plastic materials and is intended to be disposable. However, the needle guide 2 may be constructed of stainless steel and hence may be sterilized and reused.

FIGS. 2–7 illustrate the members which are assembled into the preferred embodiment needle guide 2 to accomplish the advantages provided by the invention. The band 8 is provided with protrusion 10 along its circumference such that protrusion 10 extends outwardly from band 8. Protrusion is shaped to have a tapered body 50 having a top wall 52 which extends further from band 8 than its lower wall 54.

A mounting body 14 fits onto protrusion 10 when desired, by receiving protrusion 10 between the spaced apart rails 16, 18 of mounting body 14. Rails 16, 18 have rear edges 64 which incline corresponding to the taper of protrusion 10 such that protrusion 10 may fit snugly in channel 66 formed by rails 16, 18.

Flange 106 of mounting body 14 is provided with an opening 20 into which a male snap member on base member 24 (not shown) may be received when base member 24 is fixed to mounting body 14. Other mechanical attachment means may be used to fix base member 24 to mounting body 14, or these two members may be fabricated as a single unit. Base member 24 is provided with a hollow 78 on its first side 68 into which the upper section 70 of mounting body 14 is received.

Figure 6:
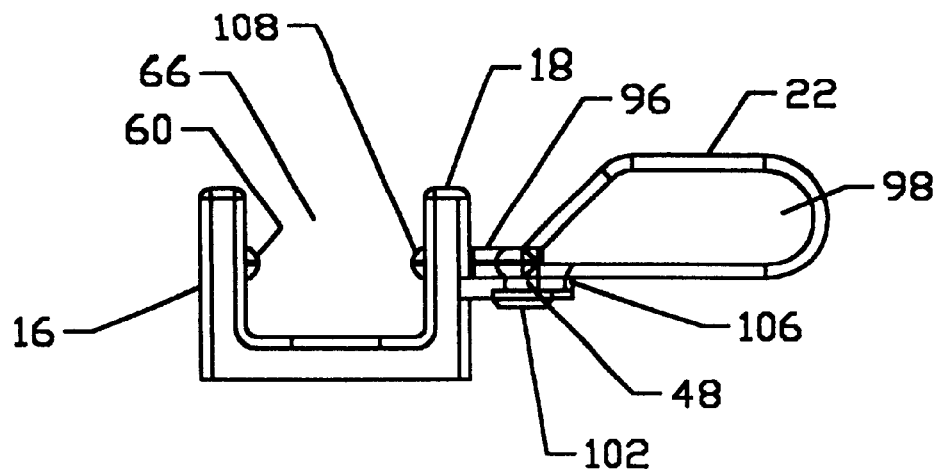
FIG. 6 is top plan view of the mount body of the invention with the lock lever installed thereon.
Figure 7:
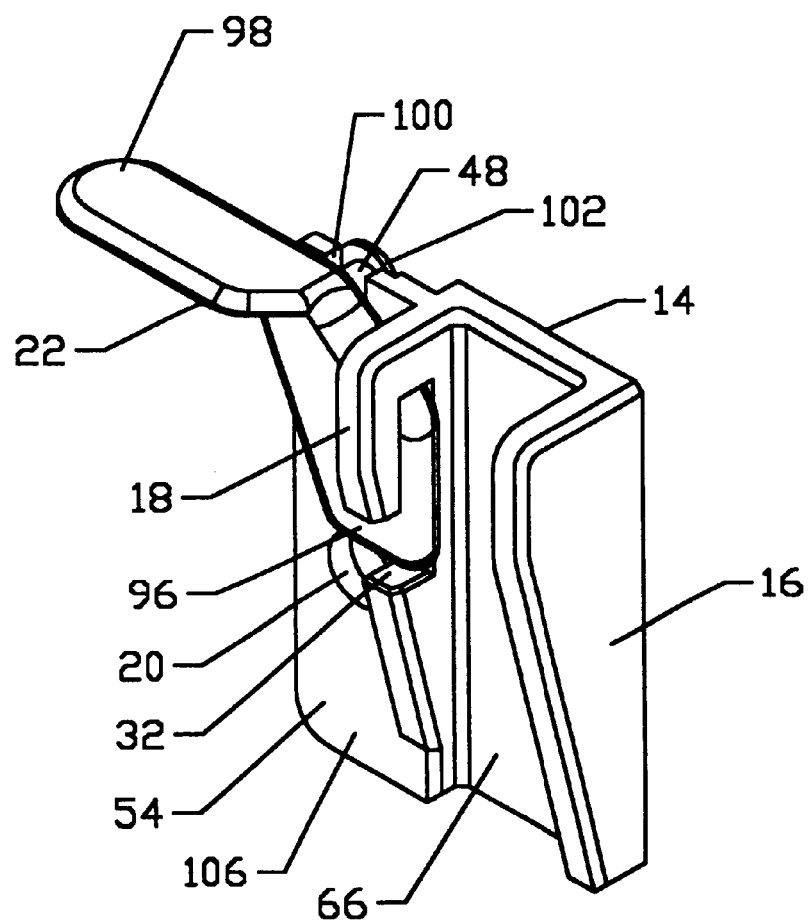
FIG. 7 is a rear right perspective of the mount body of the invention with the lock lever installed thereon in its locked position.

Referring particularly to FIGS. 6 and 7, detail of the first side 56 of mount body 14 can be seen to include the lock lever 22 mounted to mount body 14 and rotatable thereon. Specifically, in the preferred embodiment, mount body 14 includes first rail 16 spaced apart from generally parallel second rail 18, leaving channel 66 therebetween for receiving the body 50 of protrusion 10. A notch 100 is provided in the top edge of flange 106 into which may be snapped a pin 48 which depends from lock lever 22. Pin 48 has an enlargement or knob 102 at its free end to retain lock lever adjacent flange 106. Lock lever 22 may rotate about its pin 48 within notch 100 over a range limited in a counterclockwise direction (as seen in FIG. 7) by the slot 32 of second rail 18. Blade 96 of lock lever 22 may enter slot 32 thereby encroaching into channel 66 at its free edge 108. A ridge 60 is disposed upon first rail 16 within channel 66 opposing slot 32 of second rail 18. When mount body 14 is to be placed upon protrusion 10, lock lever 22 is rotated clockwise (as viewed from first side 56) to remove blade 96 from slot 32. Once protrusion 10 is received in channel 66, lock lever 22 is rotated so that blade 96 impinges on the side of protrusion 10. Lock lever 22 is manipulated by movement of lock handle 98. A detent may be installed on lock lever 22 to be received in a recess on the face of flange 106, in order to restrict the rotation of lock lever 22 about pin 100.

Referring again to FIGS. 2–5, opposing wall 72 of base member 24 is provided with a planar face 74 which diametrically opposes hollow 78. Opposing wall 72 also includes an recess containing face 76 lateral to planar face 74. Recess containing face 76 is provided with a shallow rectangular recess 80 into which one wing 30 of spring element 28 may be received.

Opposing wall 72 of base member 24 includes spaced apart ears 42 disposed generally midway laterally along opposing wall 72. Each of ears 42 is provided with an inwardly directed cylindrical indentation 82 facing opposingly the cylindrical indentation 82 of the other ear 42.

Gauge top 34 includes a retention end 84 and a handle end 86 on opposing sides of central segment 88 on which axle stubs 44 are mounted. The opposing cylindrical indentations 82 of ears 42 are disposed to receive axle stubs 44 on gauge top 34 such that axle stubs 44 and cylindrical indentations 82 may cooperate to provide a hinge around which gauge top 34 may rotate. Alternate structures for the pivot axle may be employed.

Retention end 84 of gauge top 34 is provided with V-shaped or triangular groove 38 which extends the vertical length of gauge top 34. Alternatively, groove 38 may be of rectangular or semi-cylindrical shape. When gauge top 34 is fixed to base 24 by snapping axle stubs 44 of gauge top 34 into cylindrical indentations 82 of base 24, triangular groove 38 abuts planar face 74 of base 24 and an open ended passageway 90 is formed between triangular groove 38 and planar face 74 of base 24. Spring 28 is captured between base 24 and gauge top 34 and biases retention end 84 of gauge top 34 toward planar face 74 of base 24. Alternatively, spring 28 may be incorporated in base 24 or gauge top 34 or permanently fixed to one of them. Handle end 86 of gauge top 34 includes lever 36 which is angularly displaced from recess containing face 76 of base 24 when gauge top 34 is fixed to base 24. Lever 36 may be curved upward to provide a convenient area for placement of a forefinger thereon. Because lever 36 is spaced from recess containing face 76 and urged therefrom by spring 28, finger pressure urging lever 36 toward recess containing face 76 causes gauge top 34 to pivot about the hinge created by the interaction of indentations 82 and axle stubs 44. When needle guide 2 is operated like an alligator clip or spring-type clothes pin, triangular groove 38 separates from planar face 74 and a needle located within passageway 90 may easily be separated from needle guide 2 and the transducer probe 4 to which needle guide 2 is attached.

The conical or funnel shaped opening 40 in top side 92 is coaxial with triangular groove 38 such that the insertion of the tip of a biopsy needle 12 is facilitated by the centering action of the funnel shaped opening 40 of the passageway 90.

Lever 36 may be marked with a part number or other indicator 94 which may indicate the size of needle 12 which may be passed through the passageway 90. Should a larger or smaller needle need to be substituted for the first needle chosen, it can be seen that gauge top 34 may be disconnected from base member 24 without tools and an alternative gauge top 34 may be attached to base 24, with such alternative gauge top 34 having a triangular groove 38 which has a different width and depth.

In preparation for a biopsy, amniocentesis, or other puncturing procedure, the physician is provided with a fully assembled needle guide 2 ready for attachment to an elastic mounting bracket 6 already attached to a transducer probe 4. The indicator 94 informs the physician whether the needle guide 2 is provided with the proper sized passageway 90 for the gauge of needle 12 to be used. Once the needle guide 2 has been mounted to the protrusion 10 of the band 8, the procedure may be commenced.

It can be easily understood that a physician may place the ultrasound transducer probe 4 equipped with a mounted needle guide 2 against the skin of the patient on whom a procedure is to be performed. Once the target (tumor to be biopsied or site to be drained) is visualized on the ultrasound system monitor, a biopsy needle or cannula may be inserted into the conical opening 40 of passageway 90 and directed therethrough toward the patient's body. Once a puncture has been accomplished, the needle 12 may be inserted toward the identified target to intersect therewith. Once placed, the lever 36 of the needle guide 2 may be depressed, allowing the transducer probe 4 and needle guide 2 to be separated from the sited needle 12 by drawing the transducer probe 4 and attached needle guide 2 laterally such that planar face 74 is passed along the needle 12 and the needle 12 is freed from the needle guide 2.

What is claimed is:

1. A needle guide for use with an ultrasound transducer probe comprising a mounting strap for mounting to said transducer probe, said mounting strap having a protrusion thereon, a mounting body having a channel to receive said protrusion of said mounting strap, retaining means to retain said channel to said protrusion, a base member selectively fixed to said mounting body, said base member having a first face thereon, said face directed away from said mounting body, a retaining member selectively hingedly mountable to said base member, said retaining member comprising a side facing said first face of said base member, said retaining member having a lever extending therefrom, said side having a groove extending the vertical length thereof, a spring interposed between said lever and said base member urging said side into abutment on said first face, said groove and said first face forming an open-ended passageway therebetween, said lever operative to cause said retention member to pivot about said hinge connection with said base member whereby when said lever is depressed, said side of said retention member separates from its abutment with said first face of said base member.

2. The needle guide of claim 1 wherein
said mounting strap is an endless flexible loop.
3. The needle guide of claim 1 wherein
said mounting strap is an endless elastic band.
4. The needle guide of claim 1 wherein
said mounting strap is a belt having opposing ends interconnectable by hook and loop fasteners.
5. The needle guide of claim 1 wherein
said groove of said side of said retaining member is triangular in cross section.
6. The needle guide of claim 1 wherein
said groove having an upper end,
said first side having a semiconical recess therein,
said recess coaxial with said groove and disposed at the upper end thereof.
7. The needle guide of claim 1 wherein
said mounting strap is an endless elastic band,
said groove of said side of said retaining member is triangular in cross section,
said base member having a pair of spaced apart ears depending from said first face thereof,
said ears having recesses vertically disposed therein,
each of said recesses opposing the other of said recesses,
said retaining member having an intermediate region between said first side and said lever thereof,
said intermediate region having cylindrical stubs extending coaxially therefrom,
said stubs receivable in said cylindrical recesses of said ears,
said retaining member pivotable about said coaxial stubs.
8. The needle guide of claim 7 wherein
an indicator is displayed upon said lever to indicate the size of needle receivable by said needle guide.
9. An improved needle guide for operation with an ultrasound transducer probe comprising
a strap for selective surrounding attachment to the ultrasound transducer probe,
said strap conformable to the shape of said ultrasound transducer probe,
said strap having a protruding body extending therefrom,
a base having a bracket mountable to said protruding body,
the base including a substantially vertical open ended passageway therethrough for receiving a needle therewithin,
said passageway disposed to direct said needle toward a target field for imaging by said ultrasound transducer probe.
10. The needle guide of claim 9 wherein
said strap is an endless elastic band which snugly conforms to the shape of said ultrasound transducer probe.
11. The needle guide of claim 9 wherein
said passageway has an upper opening having formed thereon a funnel coaxial with said passageway.
12. The needle guide of claim 9 wherein
said base comprises a first member selectively abutting a second member,
said first member having a planar face thereon,
said second member having a surface having an elongate groove generally vertically disposed thereon,
said planar face and said elongate groove cooperating to form said passageway when said first member abuts said second member, said planar face urged toward said surface by a spring.

13. The needle guide of claim 9 wherein said bracket comprises a pair of spaced apart rails defining a channel therebetween, said channel snugly receivable upon said protrusion of said strap, said bracket having a rotatable lever with a blade and a handle, one of said rails having an elongate opening therethrough, said blade selectively receivable within said elongate opening, said blade impinging upon said protrusion when said blade is received within said elongate opening.

14. The needle guide of claim 12 wherein said groove of said surface of said second member having an upper end, said surface having a semiconical recess therein, said recess coaxial with said groove and disposed at the upper end thereof.

15. An improved needle guide apparatus for selective attachment to an ultrasound transducer probe communicatingly attached to an ultrasound monitoring system comprising a generally planar base member having a first side and a second side, said first side of said base member having a planar face thereon, said second side mountable to said ultrasound transducer probe, a guide member comprising a plate and a lever depending from said plate, said plate having a first face opposing said planar face of said base member, said first face of said guide member having a generally vertical groove thereupon, said first face abuttable with said planar face, a spring disposed between said base member and said guide member, said spring urging said first face into abutment with said planar face, said lever manually operable to selectively separate said first face of said guide member from said planar face of said base member.

* * * * *